United States Patent
Strobel et al.

(10) Patent No.: US 7,244,720 B2
(45) Date of Patent: Jul. 17, 2007

(54) SOLUBLE FORMS OF AMOXICILLIN AND TREATMENT OF ANIMALS

(75) Inventors: Michael Strobel, Northfield, MN (US); Pat Soderland, New Prague, MN (US)

(73) Assignee: Pharmaceutical Solutions, Inc., Northfield, MN (US)

( * ) Notice: Subject to any disclaimer, the term of this patent is extended or adjusted under 35 U.S.C. 154(b) by 178 days.

(21) Appl. No.: 10/216,204

(22) Filed: Aug. 12, 2002

(65) Prior Publication Data

US 2003/0022880 A1 Jan. 30, 2003

Related U.S. Application Data

(62) Division of application No. 09/731,906, filed on Dec. 8, 2000, now Pat. No. 6,492,354, which is a division of application No. 09/251,154, filed on Feb. 17, 1999, now Pat. No. 6,225,304.

(51) Int. Cl.
*A61K 31/43* (2006.01)
*A61K 31/194* (2006.01)
*A61K 8/362* (2006.01)
*A61K 8/02* (2006.01)

(52) U.S. Cl. ............. 514/199; 514/574; 514/974
(58) Field of Classification Search ........... 514/199, 514/574, 974
See application file for complete search history.

(56) References Cited

U.S. PATENT DOCUMENTS

| | | | | |
|---|---|---|---|---|
| 5,670,170 A | * | 9/1997 | Grimmett et al. | 424/489 |
| 6,225,304 B1 | * | 5/2001 | Strobel et al. | 514/199 |
| 6,492,354 B2 | * | 12/2002 | Strobel et al. | 514/199 |

OTHER PUBLICATIONS

*Pharmaceutical Solutions, Inc. v. Vitamax et al.* Complaint filed on Aug. 1, 2005 in The United States District Court for the District of Minnesota Case No. 05-1621 DWF/JSM.

* cited by examiner

*Primary Examiner*—Ardin H. Marschel
*Assistant Examiner*—Donna Jagoe
(74) *Attorney, Agent, or Firm*—Crowell & Moring; John W. Ryan

(57) ABSTRACT

A solid mixture or aqueous solution of amoxicillin antibacterial agent with a material that aids in its dissolution in water to render it ingestive and palatable.

13 Claims, No Drawings

SOLUBLE FORMS OF AMOXICILLIN AND TREATMENT OF ANIMALS

This application is a Divisional of U.S. patent application Ser. No. 09/731,906, filed Dec. 8, 2000, now U.S. Pat. No. 6,492,354 which is a Divisional of U.S. patent application Ser. No. 09/251,154, filed Feb. 17, 1999, now U.S. Pat No. 6,225,304 in the name of Michael STROBEL and Patrick SODERLUND, which is incorporated herein by reference.

FIELD OF THE INVENTION

The instant invention relates to a readily water-soluble ingestible form of amoxicillin formed by the reaction with a hydrocylatedpolycarboxylic acid of the formula

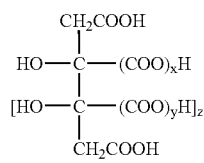

where x and y are 0 or 1 and z is 0 to 3. This water-soluble form possesses palatability and unique storage stability. The water-soluble form of the invention allows feeding orally to animals, as well as humans, without loss of antibiotic benefits. This water-soluble form is derived from an anhydrous solid, particulate mixture of the amoxicillin and the hydroxylatedpolycarboxylic acid.

BACKGROUND OF THE INVENTION

Penicillin constitutes one of the most important and widely-used groups of antiobiotics. Although numerous other antimicrobial groups of antiobiotics have been produced since the first penicillin became available, penicillins and new derivatives of the basic penicillin nucleus are still being widely researched and, when proved to be successful, produced in large quantities. Many of the new derivative compounds have unique advantages making them the preferred drug of choice for the treatment of infectious diseases. One such compound is amoxicillin which is a member of the class of aminopenicillins. One unique advantage of amoxicillins is their efficacy toward a much broader spectrum of infections when compared to penicillins.

More specifically, amoxicillion is a widely employed antibiotic having the following formula:

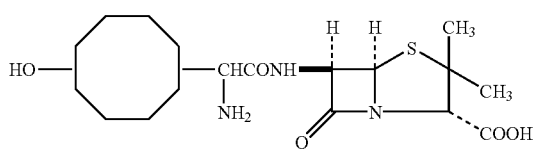

It is effective against a wide range of gram-negative and gram-positive bacteria. It is used in the treatment of infections of the urinary and respiratory tracts and of skin and soft tissues due to sensitive pathogens. In treating humans, it is typically administered orally, e.g., in a tablet form or an oral suspension.

The treatment of animals with an amoxicillin is fraught with many difficulties. For example, injecting amoxicillin is time consuming and costly, especially with large numbers of animals are involved. It is also potentially hazardous to the animal because a needle can break off in the animal and/or create an infective injection site. Feeding even a farmyard animal, let alone a wildlife species, with an amoxicillin tablet is minimally a taxing chore.

Amoxicillin slowly dissolves in the acidic environment of the normal stomach, e.g., pH of less than 3.0. It is available in the form of suspensions and tablets.

Amoxicillin hydrochoride and amoxicillin monohydrate are readily dissolved in forms which are 50% neutrally charged. The neutrally charged form has limited solubility compared to the ionized drug forms.

Amoxicillins are somewhat less active than penicillin G against gram-positive cocci sensitive to the latter agent. The meningococci and *L. monocytogenes* are sensitive to the drug. Many pneumococcal isolates have varying levels of resistance to ampicillin. Penicillin-resistant strains should be considered ampicillin/amoxicillin resistant. *H. influenzae* and the virdians group of streptococci usually are inhibited by very low concentrations of ampicillin. However, strains of type b *H. influenzae* that are highly resistant to ampicillin have been recovered from children with meningitis. It is estimated that 25% to 30% of cases of *H. influenzae* meningitis are now caused by ampicillin-resistant strains. Enterococci are about twice as sensitive to ampicillin, on a weight basis, as they are to penicillin G (MIC for ampicillin averages 1.5 mg/ml). Although most strains of *N. gonorrhoeae, E. coli, P. mirabilis , Salmonella*, and *Shigella* highly susceptible when ampicillin was first used in the early 1960s, an increasing percentage of these species is now resistant. From 30% to 50% of *E. coli*, a significant number of *P. mirabilis*, and practically all speices of Enterobacter are presently insensitive. Resistant strains of *Salmonella* (plasmid mediated) have been recovered with increasing frequency in various parts of the world. Most strains of *Shigella* are now resistant. Most strains of *Pseudomonas, Klebsila, Serratia, Acinetobacter*, and indole-positive *Proteus* also are resistant to this group of penicillins; these antibiotics are less active agains *B. fragilis* than is pencillin G. However, concurrent admistration of a β-lactamase inhibitor such as clavulante of sulbacam markedly expands the spectrum of activity of these drugs.

Amoxicillin, a penicillinase-susceptible semi-synthetic pencillin, is a close chemical and pharmacological relative of ampicillin. The drug is stable in acid and is designed or oral use. It is more rapidly and completely absorbed from the gastrointestinal tract than is ampicillin, which is the major difference between the two. The antimicrobial spectrum of amoxicillin is essentially identical to that of ampicillin, with the important exception that amoxicillin appears to be less effective than ampicillin for shigellosis (Neu, 1979).

Peak concentrations of amoxicillin (AMOXIL, others) in plasma are two to two and one-half times greater for amoxicillin than for ampicillin after oral administration of the same doses; they are reached at 2 hours and average about 4 μg/ml when 250 mg is adminstered. Food does not interfere with absorption. Perhaps because of more complete absorption of this congener, the incidence of diarrhea with amoxicillin is less than that following administration of ampicillin. The incidence of other adverse effects appears to be similiar. While the half-life of amoxicillin is similar to that for ampicillin, effective concentrations of orally administered amoxicilin are detectabale in the plasma for twice as long as with ampicillin, again because of the more complete absorption. About 20% of amoxicillin is proteinbound in plasma, a value similar to that for ampicillin. Most of a dose of the antibiotic is excreted in an active form in the urine. Probenecid delays excretion of the drug. (See Gordon et al., 1972)

U.S. Pat. No. 5,725,879 (Daoudal) describes a veterinary tablet for promoting ingestion of medicinal substances by domestic animals, especially by cats. U.S. Pat. No. 5,725,879 fails to disclose that the composition can be orally administered either directly or through drinking water.

U.S. Pat. No. 5,643,902 (Cracknell) describes a formulation comprising amoxycillin or a veterinary acceptable derivative thereof, clavulanic acid or a veterinary acceptable derivative thereof, and a veterinarily acceptable carrier is used in the treatment of farrowing fever and/or bacterial pneumonia in pigs. U.S. Pat. No. 5,643,902 fails to disclose or teach a water-soluble form of the amoxicillin compound useful in treating animals, as well as humans, without loss of antibiotic benefits. Moreover, the preferred veterinarily acceptable carriers include acceptable oils such as mineral oils or fractionated cocunut oil. And finally, the formulation is administered to the animal by intramuscular injection.

U.S. Pat. No. 4,145,429 (Clarke) describes a fluid pharmaceutical formulation for oral administration to animals comprising a medicament, an edible oil, and an oleophilic clay (thickening agent). For the same reasons given above, U.S. Pat. No. 4,145,429 fails to disclose or teach a water-soluble form of the amoxicillin compound useful in treating animals, as well as humans, without loss of antibiotic benefits. Again, an oil-based formulation teaches away from applicants' present invention U.S. Pat. No. 3,940,483 (Dursch) describes dry solid antibiotic compositions of a solid acidic, basic or amphoteric antibiotic, inclusive of amoxicillin, such as cephalexin, and a suitable solid basic or acidic additive, for reconstitution as injectables upon addition of water. According to this patent, antibiotics of limited water solubility are formulated for parenteral application either as aqueous suspensions, or by preparing water soluble derivatives (e.g., salts, esters of complexes) of the parent compound, which upon parenteral administration are either in equilibrium with the parent compound, or which are transformed back into the parent compound in the patient's system. The patentee states that a solids in suspension "severely limits the mode of parenteral administration." The patentee also states that the pharmaceutically acceptable solid derivatives are frequently prepared with significant yield losses. The derivatives are alleged to resist isolation in suitable form altogether. The patentee overcomes the prior art deficiencies by premixing antibiotics of limited water solubility which are either acidic, basic, or amphoteric in nature, with a suitable solid additive to form a dry mixture. On addition of water to the dry mixture, physiologically acceptable solutions of water soluble salts of the antibiotic are formed in situ and can be administered without delay. The patentee illustrates antibiotics such as penicillins, e.g., ampicillin, amoxicillins, and the like, as amphoteric antibiotics that can be dry blended. According to this patent, "suitable additives for amphoteric antibiotics may be either acidic or basic character." Illustrative of suitable acidic additives are alkali metal hydrogen sulfates, and organic acids like citric acid, tartaric acid or maleic acid. There is no explicit indication of the amount of acid compound that is to be used in the dry mixture. In this regard, the patentee states: "The selected solid additive is usually employed in an amount just sufficient to assure complete dissolution of the antibiotic upon addition of a small volume of water. This amount may well be less than the stoichiometric quantity required for complete conversion to a salt. Herein lies another advantage of the present invention over the use of pre-formed salts; frequently, less extreme conditions of acidity or basicity are required for complete dissolution and superior stability of such solutions can be expected. For example, 95 mole-% of sodium carbonate is sufficient to dissolve ampicillin at pH 8.3, whereas an aqueous solution of pre-formed sodium ampicillin shows about pH 9.5." The examples of the patent show dry mixtures that on dissolution in water result in pH's as low as 2 and as high as 9.7. The patent is unconcerned with ingestion of the antibiotic or for forming a palatable dry mixture that can be ingested by the animal.

La Via et al., U.S. Pat. No. 4,235,900, combine arginine and cephradine to form a solid mixture that is soluble in water. This forms an injectable solution.

French patent publication 2 308 368 describes a lysine salt of cephradine that can be administered orally as well as by intramuscular or intravenous injection. Such a lysine salt dissolved in water has been found to be unpatentable.

There is a need for stable liquid forms of amoxicillin, that can be orally administered (i.e., ingested) via an animal's drinking water without rejection by the animal because of the bad taste imparted by the liquid amoxicillin. Such a palatable form of amoxicillin allows large scale dosage-controlled treatment of animals with the antibiotic.

The Invention

This invention relates to the formation of solid mixtures and aqueous solutions of amoxicillin antibacterial agents with a material that aids in its dissolution in water to render it ingestive and palatable. The amoxicillins used in the practice of this invention are those that are antibacterials to the bacteria in the animal that is being treated. The term "anhydrous," when used to characterize the solid mixture of the amoxicillin, does not exclude bound water in the form of hydrated water bound to the amoxicillin. For the purposes of this invention, even when a amoxicillin hydrate such as cephalexin monohydrate is provided in the mixture, the mixture is still regarded to be anhydrous. The reason for this characterization is based on the fact that the hydrate form of the amoxicillin remains solid and dry and can be formed into the mixture without forming a solution.

The solid essentially anhydrous mixture contains an amoxicillin and a hydroxypolycarboxylic acid of the formula:

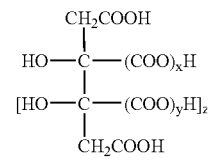

where x and y are 0 or 3 and z is 0 to 3, in appropriate amounts so that upon addition to water, there is an apparent reaction to form a palatable soluble "hydroxyacylated amoxicillin," that is, a water soluble salt of the amoxicillin and the hydroxypolycarboxylic acid. Suitable hydroxylatedpolycarboxylic acids include 2-hydroxy n-propyl 1,2,3-tricarboxylic acid (also known as citric acid), 2,3-diyroxyl n-butyl 1,4-dicarboxylic acid (also known as tartaric acid), 2-hydroxyl n-propyl 1,3-dicarboxyl acid (also known as 2-hydroxy malonic acid), 2-hydroxyl n-butyl 1,2,4=tricarboxylic acid, 2-hydroxy n-butyl 1,3,4=tricarboxylic acid, glucaric acid, and the like.

An important facet of the invention is the weight ratio of hydroxypolycarboxylic acid to the amoxicillin in the mixture. It has been determined that the weight ratio of anhydrous solid hydroxypolycarboxylic acid to solid amoxicillin (typically in the hydrate form) should be at least about 5 to 1, preferably at least 5.5 to 1, most desirably about 6 to 1, in the mixture in order to readily form, in combination with tap, deionized or distilled water, a palatable solution that can be fed to animals without rejection. The highest weight ratio of hydroxypolycarboxylic acid to amoxicillin may be about 9 to 1, though it is preferred to keep the weight ratio below about 6 to 1 of hydroxypolycarboxylic acid to amoxicillin. If the ratio of hydroxypolycarboxylic acid to amoxicillin is too high (greater than 9 to 1), the stability of the resulting preparation is compromised and the amoxicillin breaks down to less than 25% activity by 24 hours. At a lower weight ratio, the resultant amoxicillin and hydroxypolycarboxylic acid mixture does not form a solution. In all cases tested, when attempting to form a solution from a hydroxypolycarboxylic acid/amoxicillin mixture having a weight ratio less than 4 to the extent a solution is formed, the solution is clearly unpalatable.

In addition, in order to form a palatable aqueous solution of the hydroxyacylated amoxicillin, the hydroxyacylated amoxicillin solution has a pH of about 3.0 to as high as about 4.0, preferably from about 3.3 to about 3.8.

To enhance the palatability of the solution, one may add flavorings and/or artificial sweeteners such as cyclohexylsulfamic acid, saccharin (o-benzosulfimide), and Aspartame (i.e., L-Aspartyl-L-phenylalanine methyl ester) sold as Nutrasweet® artificial sweetener, and the like, in small amounts that are sufficient to enhance the palatability of the hydroxyacylated amoxicillin solution. If the animals would not be adversely affected by inclusion of sugar in the formulation, then sugar can be used to sweeten the solution. In actual practice, the sweetener and the flavoring are added in amounts that overcome the natural bad taste of the amoxicillins that is not fully mitigated by the presence of the hydroxypolycarboxylic acid. It has been determined that pigs favor strawberry and licorice flavorings.

The invention can be employed to treat all forms of domestic animals, such as livestock, e.g., pigs (including swine), beef and dairy cattle, horses, poultry (especially chickens and turkeys), sheep, and dogs, cats, and the like, as well as non-domestic animals such as deer, buffalo, and the like, that are kept in herds and fed from a controlled water supply.

The dosage of the anhydrous mixture used in forming an aqueous solution of amoxicillin and hydroxylatedpolycarboxylic acid for feeding to the animals is quite broad, and should be sufficient to provide the required amount of amoxicillins prescribed by the veterinarian. As a rule, the amount of the anhydrous preparation of amoxicillin and hydroxylatedpolycarboxylic acid that is dissolved into water for feeding the animals should provide about 2 to about 15, preferably from about 5 to about 10, milligrams of the amoxicillin for each pound of weight of the animals being treated.

The invention allows for the preparation of dry anhydrous mixtures of the amoxicillins and the hydroxypolycarboxylic acid in the weight ratio of 5.0 to 9.0 of the hydroxypolycarboxylic acid to 1 of the amoxicillin. The mixture may contain from about 0.1 to about 5 weight percent of a flavoring and from about 0.1 to about 10 weight percent of an artificial sweetener. In special situations, greater and smaller amounts of the hydroxypolycarboxylic acid, flavoring and artificial sweetener can be used to advantage to achieve the objectives of this invention. The anhydrous mixture is stable and can be kept for an infinite period of time without deterioration. Contrary to the normal attributes of prior art acidic solutions of amoxicillins, the solutions of the invention, made by dissolving the amoxicillin and the hydroxypolycarboxylic acid in water, have remarkable storage stability as compared to non-acidified amoxicillins and the like. These solutions can be kept for as long as 7 days, at refrigeration conditions of about 7° C., without deterioration or separation (e.g., precipitation of amoxicillin).

The invention substantially enhances the uptake of amoxicillins in pigs compared to the non-solubilized form as disclosed in an article entitled "Bioavailability of Amoxycillin in Pigs" in the Journal of Veterinary Pharmacology and Therapeutics, Volume 21, No. 1, 1998, pp. 41-46. The present invention allows oral use without the addition of an injectable treatment.

The test was carried out at 5 mg/# Administered Dosage with a 98% uptake from the gut allowing one to achieve greater Serum levels and use reduced dosages with the same effect.

The mixing of the solid particulate amoxicillin and the solid particulate hydroxypolycarboxylic acid, with or without flavoring and sweetener, is not difficult to achieve. Any method and equipment that is effective in making a powdered mixture can be used in the practice of this invention to produce the anhydrous powder mixture of the amoxicillin and the hydroxylatedpolycarboxylic acid. For example, small packets of the mixture can be put into a plastic bag, typically one made of polyethylene, or polyvinyl chloride-vinylidene chloride copolymer of Mylar® (a film form of polyethyleneterephthalate), and the like. The mixtures can be made in such bags by separately feeding solid particulate amoxicillin and solid particulate hydroxylatedpolycarboxylic acid. Then the ingredients in the bag can be worked by hand to mix the particulates into an essentially homogeneously distributed mixture. The particulates can be mixed in large and small scale mixing equipment. They can be mixed in a household cake mixer, a large scale Banbury Mixer, large and small paddle mixers, and the like.

The dry (anhydrous) solid mixture of is preferably in the form of an intimate mixture of the amoxicillin and the hydroxypolycarboxylic acid particles. Preferably, the amoxicillin and the hydroxypolycarboxylic acid are each in the form of ready dissolvable powders. Such powders may be termed as fine grain powders comparable to granular or powdery sugar. The degree of blending of these powders is not critical so long as the right proportions of each component is dissolved in the body of water that is used in forming the solution comprising the amoxicillin and the hydroxypolycarboxylic acid. The key to blending and aliquoting the blend is to assure that the proper concentration of each component is present in the aliquot when the aliquot is dissolved in a common body of water.

The dry solid mixture may be dissolved in a small concentration of water, for example, an amount of water sufficient to dissolve all of the components of the dry mixture. This solution can be a concentrate of the amoxicillin and is used as a vehicle for supplying the ingredients of the dry solid mixture of the invention in the water feed of the animals.

EXAMPLE 1

Formulation: Amoxicillin Trihydrate or other hydrated or anhydrous forms of amoxicillin mixed with an organic acid, with our without a flavoring agent and a sweetener either natural artificial. Mix 1 gram of amoxicillin Trihydrate with 5.5 to 6.5 grams of citric acid, nutrisweet and strawberry flavoring. This forms a stable mixture. This mixture is added to water in a ratio of 37.5 to 60 grams of the amoxicillin fraction plus additives to one gallon of water to produce a concentrated solution to be mixed at a rate of one ounce per gallon of drinking water to animals. This mixture will deliver a dose of 3 to 5 milligrams per pound to the target animal. Typical treatment time would be from 5 to 10 days continously.

Results of trials: The amoxicillin/organic acid mixture and Nutrisweet/Strawberry flavor-uptake in the gut and produces a stable solution. The total mixture is significantly more palatable. This mixture shows enhanced absorption over feeding the amoxicillin trihydrate directly to the animal in the dry form. This allows for a reduced dose and improved uniformity and predictability in the dosing of the drug.

Unexpected result: the predicted ratio for solubility of the organic acid and amoxicillin is 2 or 3 to 1. The actual ratio needed to form a stable solution is greater then 5.0 to 1. The practical ratio used is 6 or 7 to 1 to allow for variations in the tap water it is mixed with. To assure rapid dissolution the mixture must be throughly mixed. The mixture will dissolve completely in 5 to 10 minutes.

EXAMPLE 2

A flavored and sweetened formulation of the invention is made by thoroughly mixing 187.5 grams Amoxicillin Trihydrate with 1125 grams Citric Acid and 50 grams Nutrisweet (Aspartain) 5 grams Strawberry flavoring. This will treat 5 gallons of stock solution or 640 gallons of drinking water as consumed to supply 3 mgs to the animal. This anhydrous mixture is rapidly dissolved in water to a concentration of 37.5 grams of amoxicillin per gallon of demineralized water to form a solution having a pH of about 4.2. A comparable solution is formed by substituting an equal weight amount of tartaric acid for the citric acid.

EXAMPLE 3

Treatment of streptococcus Suis—a group of 600 pigs was divided into 2 groups of 300. Each group was side by side in a 600 animal nursery room. Group 1 (300) was treated with 3 mg/lb of amoxicillin at 35 days of age for a period of 7 days. Group 2 (300) was treated with a placebo—citric acid/nutrisweet/strawberry flavor at 35 days of age for a period of 7 days. This farm had a history of STREP Suis Type 2 occurring at 2-3 weeks of age confirmed by laboratory testing. Death loss ranged from 3 to 10 percent with poor treatment results.

Results:

| Group | # | Age at Start | Morbidity Number | Mortality Number | Chronc cells @ 50 | STREP Titre results (30 random test on each group at end of study) (+) | (−) |
|---|---|---|---|---|---|---|---|
| 1 Treated | 300 | 35d | 2 | 0 | 1 | 28 | 2 |
| 2 Placebo | 300 | 35d | 28 | 18 | 6 | 28 | 2 |

This shows that all pigs were exposed but the significant impact on morbidity and mortality occurred by the amoxicillin intervention.

EXAMPLE 4

Stability of mixture in both Conc and dilute form. Mix 1 gallon as in Example #1. Test for Active Amoxicillin at $T_0$ $T_{30}$ $T_{60}$ $T_{360}$ and $T_{1440}$ mm Results % of predidicted activity—100%=10.4 mg./ml.

| $T_0$ | $T_{30}$ | $T_{60}$ | $T_{360}$ | $T_{1440}$ |
|---|---|---|---|---|
| 10.4 | 10.4 | 10.4 | 10.35 | 10.25 |

Shows good stability over time in solution.

EXAMPLE 5

Test for ability to eliminate the Carrier State of Strep suis following treatment:
Mix per Example #1 Solution
Treat 30 pigs—30 pig control
Tonsilar Swabs pre treatment and 48 hr. post treatment—pigs housed together in same room.

| Group | # | Pretest Culture and Post S Suis | $48^{th}$ Post 7 day Tx# Pos 55 pigs |
|---|---|---|---|
| Treat | 30 | 20 | 0 |
| Control | 30 | 18 | 24 |

EXAMPLE 6

| | Water consumption affect of mixture | |
|---|---|---|
| | Group Size | Gal/day Aug over 7 days tx |
| Tx w/Citric Acid Giant/Notrict | 1000 | 618 |
| Tx w/Citric Acid only | 1000 | 500 |
| Control Water Alone | 1000 | 525 |

This confirms increased palatability of mixture. Show the addition of sweetener increase the effective dose per unit weight of the pig.

EXAMPLE 7

Treatment for Hermophilus Parasuis in finishing Gilts—wt. 250#

Marked Reduction in death loss following 5 day coarse of therapy.
Treated w/3 mg/#via water.*
Controls—placebo-double blind study followed for 14 days from start of treatment—at which time the controls were treated to stop further death loss.*

| | | | | 30 head in each Group Random | | |
|---|---|---|---|---|---|---|
| #Group | Morbidity at Start | Mortality 0–7 | Mortality 8–142 | Culture result in 7 days | in 14 days | Day Culture *Pos |
| Tx | 500 | 250 | 2 | 0 | 0 | 0 | 15 |
| Control | 502 | 250 | 21 | 12 | 21 | 24 | 14 |

Farmer did not know which is which. (Farmer unable to differentiate between models)

The invention claimed is:
1. A process for the treatment of a bacterial infection in an animal in need thereof which comprises orally administering to said animal an anti-bacterial effective amount of a amoxicillin which is in an aqueous solution comprising a hydroxypolycarboxylic acid and the amoxicillin, wherein the weight ratio of the hydroxypolycarboxylic acid to the amoxicillin is at least 5.0 to 1 and the hydroxypolycarboxylic acid has the formula

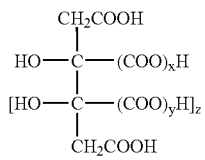

where x and y are 0 or 1 and z is 0 to 3 and wherein the aqueous solution has a pH of between about 3.0 and about 4.0.

2. The process of claim 1 wherein the weight ratio of hydroxypolycarboxylic acid to the amoxicillin is not greater than 5.0 to 1.

3. The process of claim 1 wherein the weight ratio of hydroxypolycarboxylic acid to the amoxicillin is not greater than 6.0 to 1.

4. The process of claim 1 wherein the weight ratio of hydroxypolycarboxylic acid to the amoxicillin is not greater than 7.0 to 1.

5. The process of claim 1 wherein the weight ratio of hydroxypolycarboxylic acid to the amoxicillin is not greater than 8.0 to 1.

6. The process of claim 1 wherein the aqueous solution has a pH of between about 3.3 and about 3.8.

7. The process of claim 1 wherein the aqueous solution further comprises a flavoring present in a concentration of from about 0.1 to about 5 weight percent and an artificial sweetener present in a concentration of from about 0.1 to about 10 weight percent.

8. The process of claim 1 wherein the hydroxypolycarboxylic acid is selected from the group consisting of citric acid, tartaric acid, 2-hydroxy malonic acid, 2-hydroxyl n-butyl 1,2,4-tricarboxylic acid, glucaric acid, and 2-hydroxy n-butyl 1,3,4-tricarboxylic acid.

9. A process for the treatment of a bacterial infection in an animal in need thereof which comprises orally administering to said animal an anti-bacterial effective amount of a amoxicillin which is in an aqueous solution comprising a hydroxypolycarboxylic acid and the amoxicillin, wherein the weight ratio of the hydroxypolycarboxylic acid to the amoxicillin is at least 5.0 to 1 and the hydroxypolycarboxylic acid has the formula

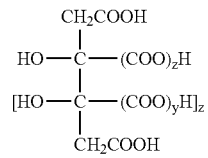

where x and y are 0 or 1 and z is 0 to 3; and wherein the anti-bacterial effective amount of a amoxicillin is determined by providing between about 2 to about 15 mg of amoxicillin per pound of the animal's weight and wherein the aqueous solution has a pH of between about 3.0 and about 4.0.

10. The process of claim 9 wherein the anti-bacterial effective amount of a amoxicillin is determined by providing between about 5 to about 10 mg of amoxicillin per pound of the animal's weight.

11. The process of claim 9 wherein the aqueous solution has a pH of between about 3.3 and about 3.8.

12. The process of claim 9 wherein the aqueous solution further comprises a flavoring present in a concentration of from about 0.1 to about 5 weight percent and an artificial sweetener present in a concentration of from about 0.1 to about 10 weight percent.

13. The process of claim 9 wherein the hydroxypolycarboxylic acid is selected from the group consisting of citric acid, tartaric acid, 2-hydroxy malonic acid, 2-hydroxyl n-butyl 1,2,4-tricarboxylic acid, glucaric acid, and 2-hydroxy n-butyl 1,3,4-tricarboxylic acid.

* * * * *